United States Patent
Coudert et al.

(10) Patent No.: US 7,312,213 B2
(45) Date of Patent: Dec. 25, 2007

(54) SUBSTITUTED BENZO[E][1,4]OXAZINO[3,2-G]ISOINDOLE COMPOUNDS

(75) Inventors: Gérard Coudert, Saint Denis En Val (FR); Franck Lepifre, Olivet (FR); Daniel-Henri Caignard, Boisemont (FR); Pierre Renard, Le Chesnay (FR); John Hickman, Paris (FR); Alain Pierre, Les Alluets le Roi (FR); Laurence Kraus-Berthier, Colombes (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 300 days.

(21) Appl. No.: 10/531,648
(22) PCT Filed: Oct. 17, 2003
(86) PCT No.: PCT/FR03/03068
§ 371 (c)(1),
(2), (4) Date: Apr. 15, 2005
(87) PCT Pub. No.: WO2004/037830
PCT Pub. Date: May 6, 2004

(65) Prior Publication Data
US 2006/0003997 A1 Jan. 5, 2006

(30) Foreign Application Priority Data
Oct. 18, 2002 (FR) .................................. 02 12964

(51) Int. Cl.
C07D 498/04 (2006.01)
A61K 31/5383 (2006.01)
(52) U.S. Cl. .................................... 514/229.5; 544/99
(58) Field of Classification Search ................. 544/99; 514/229.5
See application file for complete search history.

(56) References Cited
FOREIGN PATENT DOCUMENTS
EP 0841337 5/1998

OTHER PUBLICATIONS

Motohashi, *Pharmaceutical Society of Japan*, 1983, 103, 364-371.
Morgan, et al., *Photochemistry and Photobiology*, 2000, 71, 747-757.
International Search Report for International Application No. PCT/FR2003/03068, Feb. 23, 2004.
International Preliminary Examination Report for International Application No. PCT/FR2003/03068, Feb. 23, 2004.

*Primary Examiner*—Kahsay Habte
(74) *Attorney, Agent, or Firm*—Hueschen and Sage

(57) ABSTRACT

A compound selected from those of formula (I):

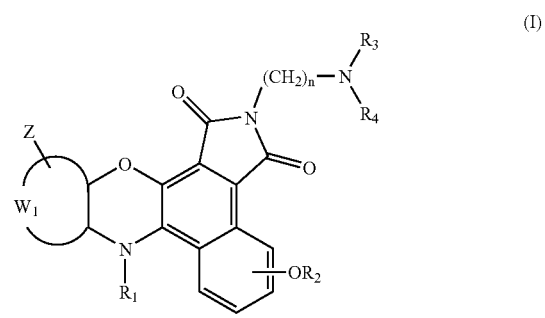

wherein:
$W_1$, with the carbon atoms to which it is bonded, represents phenyl or pyridyl,
Z represents a group selected from hydrogen, halogen, linear or branched ($C_1$-$C_6$)alkyl, aryl, aryl-($C_1$-$C_6$)alkyl, aryloxy, aryl-($C_1$-$C_6$)alkoxy, hydroxy and linear or branched ($C_1$-$C_6$)alkoxy,
$R_1$ is as defined in the description,
$R_2$ represents hydrogen or —$CH_2CH_2O$—$R_8$,
$R_3$ and $R_4$ each represents hydrogen, linear or branched ($C_1$-$C_6$)alkyl, aryl or aryl-($C_1$-$C_6$)alkyl,
n represents an integer of from 1 to 6 inclusive,
its isomers, and addition salts thereof with a pharmaceutically acceptable acid or base, and medicinal products containing the same which are useful in the treatment of cancer.

12 Claims, No Drawings

SUBSTITUTED BENZO[E][1,4]OXAZINO[3,2-G]ISOINDOLE COMPOUNDS

The present invention relates to new benzo[e][1,4]oxazino[3,2-g]isoindole compounds, to a process for their preparation and to pharmaceutical compositions containing them. The compounds of the present invention are of valuable therapeutic use owing to their anti-tumour activity.

In the literature, J. Pharm. Sciences, 1974, 63(8), pp 1314-1316 describes the synthesis of benzoxazinoquinoline compounds having anti-tumour properties. Patent Application EP 0 841 337 claims substituted 7,12-dioxabenzo[a]anthracene compounds and describes their anti-cancer properties.

The novelty of the compounds of the present invention is to be found both in their structure and in their use as anti-tumour agents. Their bioavailability is also clearly superior compared with the compounds of the prior art.

The present invention relates more specifically to compounds of formula (I):

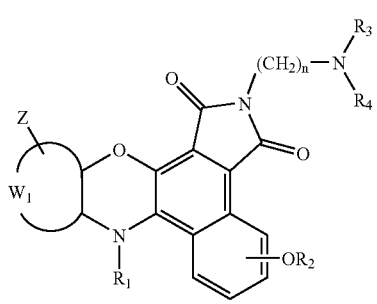

wherein:
- $W_1$ represents, with the carbon atoms to which it is attached, a phenyl group or a pyridyl group,
- Z represents a group selected from hydrogen, halogen, and the groups linear or branched $(C_1-C_6)$alkyl, aryl, aryl-$(C_1-C_6)$alkyl in which the alkyl moiety may be linear or branched, aryloxy, aryl-$(C_1-C_6)$alkoxy in which the alkoxy moiety may be linear or branched, hydroxy and linear or branched $(C_1-C_6)$alkoxy,
- $R_1$ represents a group selected from hydrogen and the groups linear or branched $(C_1-C_6)$alkyl, aryl, aryl-$(C_1-C_6)$alkyl in which the alkyl moiety may be linear or branched, —C(O)—$R_5$ and a linear or branched $(C_1-C_6)$alkylene chain, which are substituted by one or more identical or different groups selected from halogen and the groups cyano, —$OR_6$, —$NR_6R_7$, —$CO_2R_6$, —C(O)$R_6$ and —C(O)—$NHR_6$, wherein:
  - $R_5$ represents a group selected from hydrogen and the groups linear or branched $(C_1-C_6)$alkyl, hydroxy, linear or branched $(C_1-C_6)$alkoxy, aryl, aryl-$(C_1-C_6)$alkyl in which the alkyl moiety may be linear or branched and aryloxy,
  - $R_6$ and $R_7$, which may be identical or different, each represents a group selected from hydrogen and the groups linear or branched $(C_1-C_6)$alkyl, aryl and aryl-$(C_1-C_6)$alkyl in which the alkyl moiety may be linear or branched, or
  - $R_6$+$R_7$ together form, with the nitrogen atom carrying them, a monocyclic heterocycle having 5 or 6 ring members and optionally containing in the ring system a second hetero atom selected from oxygen and nitrogen.,
- $R_2$ represents a hydrogen atom or a group of formula —$CH_2CH_2O$—$R_8$ wherein: $R_8$ represents a group selected from hydrogen and the groups linear or branched $(C_1-C_6)$alkyl, aryl, aryl-$(C_1-C_6)$alkyl in which the alkyl moiety may be linear or branched, —$S(O)_t$—$R_6$ (wherein $R_6$ is as defined hereinbefore and t represents an integer of from 0 to 2 inclusive) and $T_1$-$R_9$ (wherein $T_1$ represents a linear or branched $(C_1-C_6)$alkylene chain and $R_9$ represents a group selected from halogen, cyano, —$OR_6$, —$NR_6R_7$, —C(O)H, —C(O)$OR_6$ and —C(O)$NR_6R_7$, wherein $R_6$ and $R_7$ are as defined hereinbefore),
- $R_3$ and $R_4$, which may be identical or different, each represents, independently of the other, a group selected from hydrogen and the groups linear or branched $(C_1-C_6)$alkyl, aryl and aryl-$(C_1-C_6)$alkyl in which the alkyl moiety may be linear or branched, or $R_3$ and $R_4$ together form, with the nitrogen atom carrying them, a monocyclic heterocycle having 5 or 6 ring members and optionally containing in the ring system a second hetero atom selected from oxygen and nitrogen,
- n represents an integer of from 1 to 6 inclusive, to their enantiomers, diastereoisomers, N-oxide, and to addition salts thereof with a pharmaceutically acceptable acid or base, wherein "aryl" is to be understood as meaning a phenyl, naphthyl, dihydronaphthyl, tetrahydronaphthyl, indenyl or indanyl group, each of those groups being optionally substituted by one or more identical or different groups selected from halogen, linear or branched $(C_1-C_6)$alkyl, linear or branched $(C_1-C_6)$trihaloalkyl, hydroxy, linear or branched $(C_1-C_6)$alkoxy, and amino optionally substituted by one or two linear or branched $(C_1-C_6)$alkyl groups.

Among the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic and camphoric acid etc. . . .

Among the pharmaceutically acceptable bases there may be mentioned, without implying any limitation, sodium hydroxide, potassium hydroxide, triethylamine, etc. . . .

Preferred compounds of the invention are the compounds of formula (I) corresponding more especially to formula (IA):

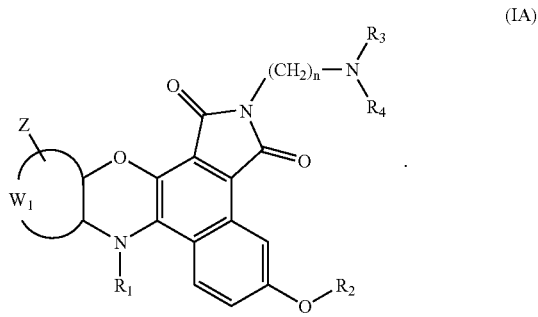

wherein $R_1$, $R_2$, $R_3$, $R_4$, $W_1$, Z and n are as defined for formula (I).

According to a second advantageous embodiment, preferred compounds of the invention are compounds of formula (I) corresponding more especially to formula (IB):

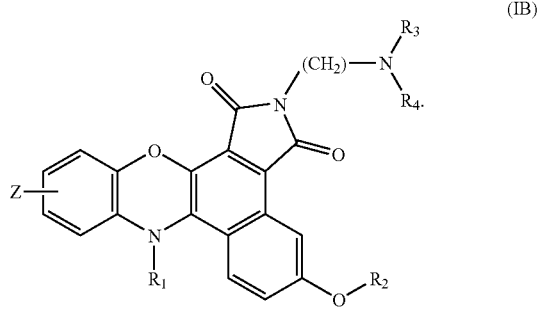

wherein $R_1$, $R_2$, $R_3$, $R_4$, Z and n are as defined hereinbefore.

According to a third advantageous embodiment, preferred compounds of the invention are compounds of formula (I) corresponding more especially to formula (IC):

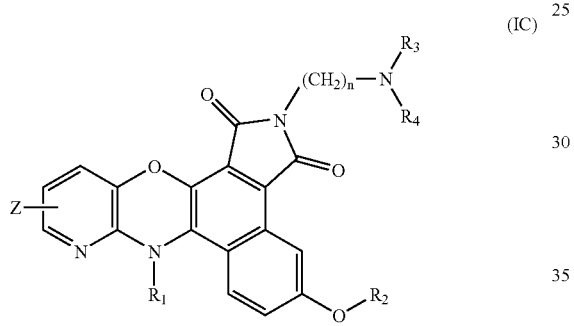

wherein $R_1$, $R_2$, $R_3$, $R_4$, Z and n are as defined hereinbefore.

In one embodiment of interest, the group Z preferred in accordance with the invention is the hydrogen atom.

In another embodiment of interest, the group $R_1$ preferred in accordance with the invention is the hydrogen atom and the group —C(O)—$R_5$ wherein $R_5$ represents more especially a hydrogen atom.

Advantageously, the group $R_2$ preferred in accordance with the invention is the hydrogen atom and the group —CH$_2$CH$_2$O—$R_8$ wherein $R_8$ represents more especially a hydrogen atom.

Very advantageously, preferred compounds of the invention are those wherein n represents the integer 2.

Especially advantageously, the groups $R_3$ and $R_4$ preferred in accordance with the invention, which may be identical or different, each represents independently of the other a linear or branched (C$_1$-C$_6$)alkyl group.

Compounds preferred in accordance with the invention are:
- 2-[2-(dimethylamino)ethyl]-5-hydroxybenzo[a]pyrrolo[3,4-c]phenoxazine-1,3-dione,
- 2-[2-(diethylamino)ethyl]-5-hydroxybenzo[a]pyrrolo[3,4-c]phenoxazine-1,3-dione,
- 2-[2-(dimethylamino)ethyl]-5-(2-hydroxyethoxy)-2,3-dihydrobenzo[a]pyrrolo[3,4-c]-phenoxazine-8-carbaldehyde-1,3-dione,
- 2-[2-(dimethylamino)ethyl]-5-(2-hydroxyethoxy)benzo[a]pyrrolo[3,4-c]phenoxazine-1,3-dione,
- 2-[2-(dimethylamino)ethyl]-5-(2-hydroxyethylmethanesulphonate)benzo[a]pyrrolo-[3,4-c]phenoxazine-1,3-dione,
- 2-[2-(dimethylamino)ethyl]-5-(2-hydroxyethoxy)benzo[e]pyrido[2',3':5,6][1,4]-oxazino[3,2-g]isoindole-1,3-dione.

The enantiomers, diastereoisomers, N-oxides, and addition salts with a pharmaceutically acceptable acid or base, of the preferred compounds form an integral part of the invention.

The invention extends also to a process for the preparation of compounds of formula (I), which is characterised in that there is used as starting material a compound of formula (II):

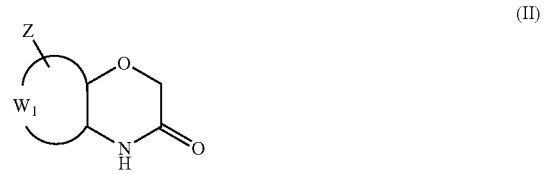

wherein $W_1$ and Z are as defined for formula (I), the amine function of which compound of formula (II) is protected by a protecting group $P_G$ well known to the person skilled in the art to yield a compound of formula (III):

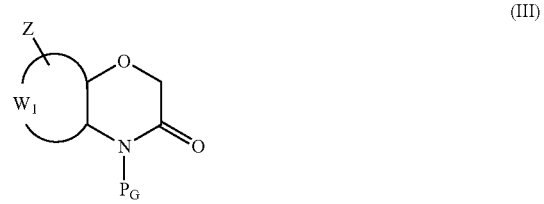

wherein $P_G$ represents a tert-butoxycarbonyl or phenoxycarbonyl group and $W_1$ and Z are as defined hereinbefore, which compound of formula (III) is treated with lithium diisopropylamide followed by diphenyl chlorophosphate to yield a compound of formula (IV):

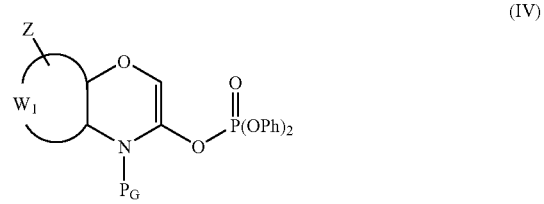

wherein $P_G$, $W_1$ and Z are as defined hereinbefore, which compound of formula (IV) is treated, in the presence of bis(triphenyl-phosphine)palladium chloride, with a compound of formula (V):

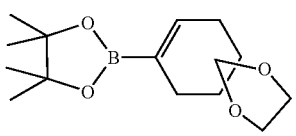

to yield a compound of formula (VI):

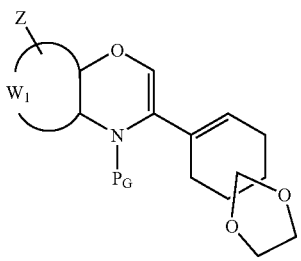
(VI)

wherein $P_G$, $W_1$ and Z are as defined hereinbefore,
which compound of formula (VI) is:
either treated under an inert atmosphere with dimethyl acetylenedicarboxylate to yield a compound of formula (VII):

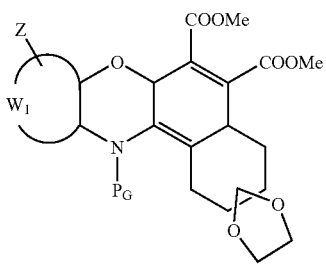
(VII)

wherein $P_G$, $W_1$ and Z are as defined hereinbefore,
which compound of formula (VII) is:
either treated with N-bromosuccinimide and benzoyl peroxide to yield a compound of formula (VIII):

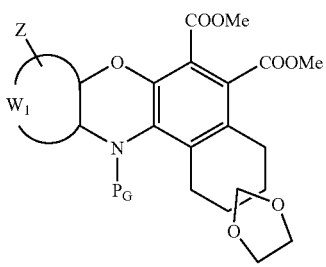
(VIII)

wherein $P_G$, $W_1$ and Z are as defined hereinbefore,
which compound of formula (VIII) is subjected to the action of hydrochloric acid to yield a compound of formula (IX):

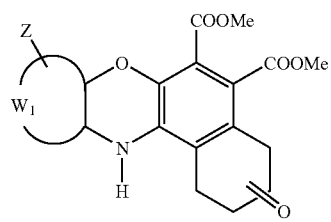
(IX)

wherein $W_1$ and Z are as defined hereinbefore,
which compound of formula (IX) is subjected to the action of di-tert-butyl dicarbonate in the presence of 4-dimethylaminopyridine to yield a compound of formula (X):

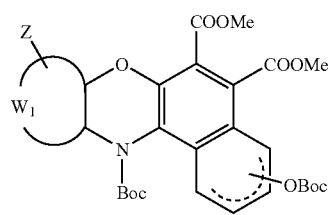
(X)

wherein ----- represents a single or double bond, Boc represents a tert-butoxycarbonyl group and $W_1$ and Z are as defined hereinbefore,
which compound of formula (X) is subjected to the action of 2,3-dichloro-5,6-dicyano-1,4-benzoquinone to yield a compound of formula (XI):

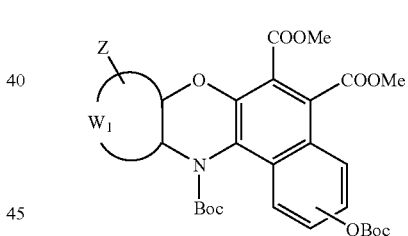
(XI)

wherein Boc, $W_1$ and Z are as defined hereinbefore,
which compound of formula (XI) is subjected to the action of sodium methanolate and is then hydrolysed to yield a compound of formula (XII):

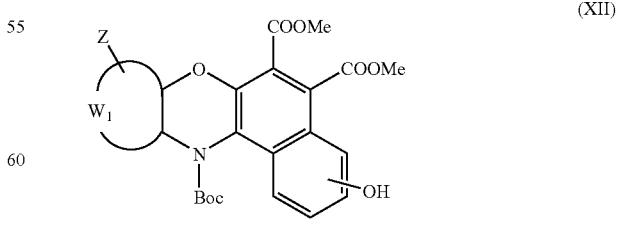
(XII)

wherein Boc, $W_1$ and Z are as defined hereinbefore,
which compound of formula (XII) is subjected to the action of a compound of formula (XIII):

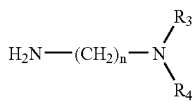

(XIII)

wherein $R_3$, $R_4$ and n are as defined for formula (I), to yield a compound of formula (I/a), a particular case of the compounds of formula (I):

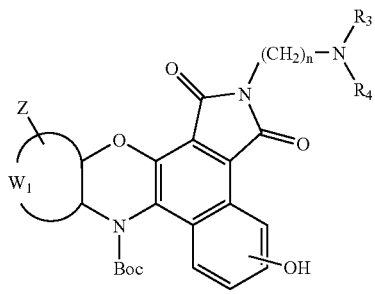

(I/a)

wherein Boc, $R_3$, $R_4$, $W_1$, Z and n are as defined hereinbefore, which compound of formula (I/a) is optionally subjected to the same reaction conditions as the compound of formula (VIII) to yield a compound of formula (I/b), a particular case of the compounds of formula (I):

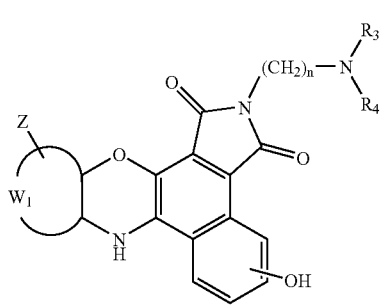

(I/b)

wherein $R_3$, $R_4$, $W_1$, Z and n are as defined hereinbefore, or subjected to the same reaction conditions as the compound of formula (X) to yield a compound of formula (XIV):

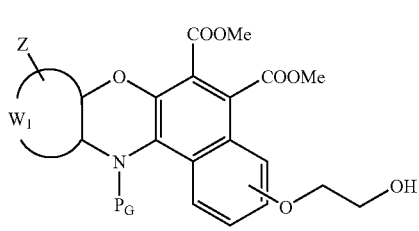

(XIV)

wherein $P_G$, $W_1$ and Z are as defined hereinbefore, which compound of formula (XIV) is subjected to the same reaction conditions as the compound of formula (XII) to yield a compound of formula (I/c), a particular case of the compounds of formula (I):

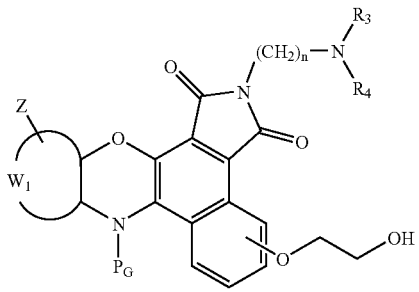

(I/c)

wherein $P_G$, $R_3$, $R_4$, $W_1$, Z and n are as defined hereinbefore, which compound of formula (I/c) is:
  either optionally subjected to the action of formic acid to yield compounds of formulae (I/d) and (I/e), particular cases of the compounds of formula (I):

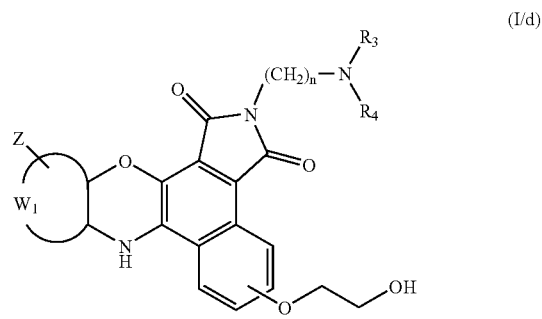

(I/d)

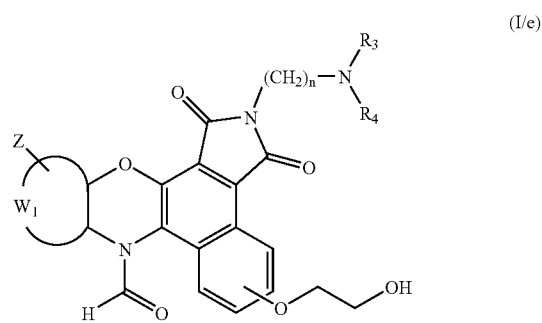

(I/e)

wherein $R_3$, $R_4$, $W_1$, Z and n are as defined hereinbefore,
  or optionally subjected to the action of a compound of formula (XV):

$$R_{8a}-G \qquad (XV)$$

wherein G represents a leaving group and $R_{8a}$, which is other than a hydrogen atom, has the same definition as $R_8$ in formula (I), to yield a compound of formula (I/f), a particular case of the compounds of formula (I):

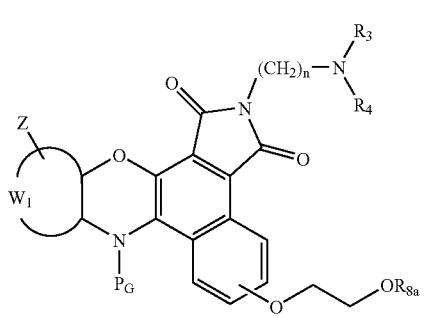

(I/f)

wherein $P_G$, $R_3$, $R_4$, $R_{8a}$, $W_1$, Z and n are as defined hereinbefore, the amine function of which compounds of formula (I/f) is optionally deprotected according to conventional methods of organic synthesis to yield a compound of formula (I/g), a particular case of the compounds of formula (I):

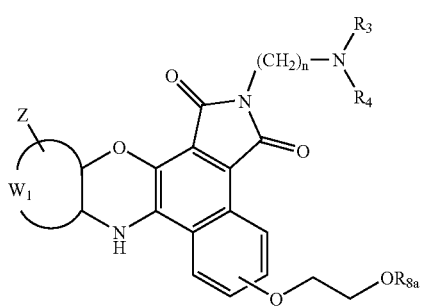

(I/g)

wherein $R_3$, $R_4$, $R_{8a}$, $W_1$, Z and n are as defined hereinbefore, the compounds of formulae (I/b), (I/d) and (I/g) constituting the compounds of formula (I/h):

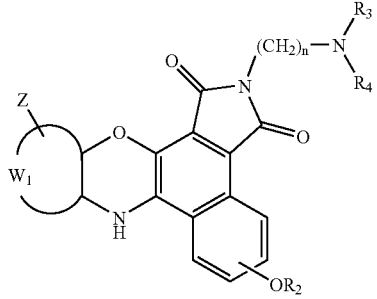

(I/h)

wherein $R_2$, $R_3$, $R_4$, $W_1$, Z and n are as defined hereinbefore, which compounds of formula (I/h) are optionally subjected to the action of a compound of formula (XVI):

$$R_{1a}-G \quad (XVI)$$

wherein $R_{1a}$, which is other than a hydrogen atom, has the same definition as $R_1$ in formula (I) and G is as defined hereinbefore, to yield a compound of formula (I/i), a particular case of the compounds of formula (I):

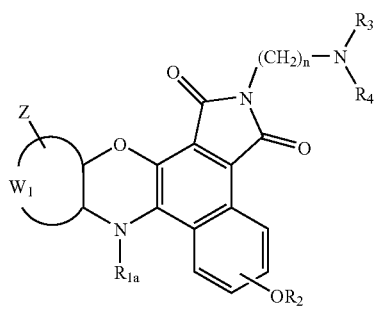

(I/i)

wherein $R_{1a}$, $R_2$, $R_3$, $R_4$, $W_1$, Z and n are as defined hereinbefore, or treated with N-methylmaleimide to yield a compound of formula (XVII):

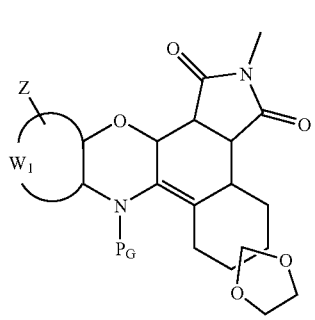

(XVII)

wherein $P_G$, $W_1$ and Z are as defined hereinbefore, which compound of formula (XVII) is subjected to the same reaction conditions as the compound of formula (VII) to yield a compound of formula (XVIII):

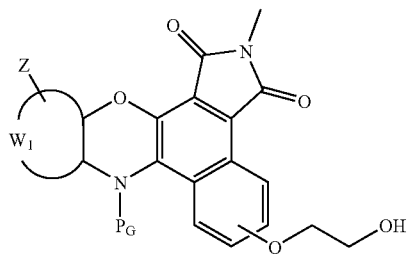

(XVIII)

wherein $P_G$, $W_1$ and Z are as defined hereinbefore, which compound of formula (XVIII) is subjected to the same reaction conditions as the compound of formula (XII) to yield a compound of formula (I/d) as described hereinbefore, the compounds of formulae (I/a) to (I/i) constituting the totality of the compounds of formula (I), which compounds are optionally purified according to conventional purification techniques, may, if desired, be separated into their different isomers according to a conventional separation technique and are, if desired, converted into their N-oxides and, optionally, into addition salts with a pharmaceutically acceptable acid or base.

The invention relates also to compounds of formula (X), (XI) and (XIV), which are synthesis intermediates for use in the preparation of the compounds of formula (I).

The compounds of formulae (II), (V), (XIII), (XV) and (XVI) are either commercially available compounds, or are compounds obtained according to conventional methods of organic synthesis readily accessible to the person skilled in the art.

The compounds of formula (I) have valuable pharmacological properties. They have an excellent in vitro cytotoxicity not only on leukaemia lines but also on solid tumour lines, and also have an action on the cell cycle and are active in vivo, on a leukaemia model. Those properties enable them to be used therapeutically as anti-tumour agents.

Among the types of cancer that the compounds of the present invention are capable of treating, the following may be mentioned without implying any limitation: adenocarcinomas and carcinomas, sarcomas, gliomas and leukaemias.

The present invention relates also to pharmaceutical compositions comprising the products of formula (I), its enantiomers, diastereoisomers, N-oxides or one of the pharmaceutically acceptable addition salts thereof with a base or an acid, on its own or in combination with one or more inert, non-toxic excipients or carriers.

Among the pharmaceutical compositions according to the invention there may be mentioned more especially those which are suitable for oral, parenteral, nasal, rectal, perlingual, ocular or respiratory administration, and especially tablets or dragées, sublingual tablets, sachets, paquets, gelatin capsules, glossettes, lozenges, suppositories, creams, ointments, dermal gels, injectable or drinkable preparations, aerosols, eye drops or nose drops.

In view of the pharmacological properties characteristic of the compounds of formula (I), the pharmaceutical compositions comprising the said compounds of formula (I) as active ingredient are thus especially useful in the treatment of cancers.

The useful dosage varies in accordance with the age and weight of the patient, the administration route, the nature of the therapeutic indication and of any associated treatments and ranges from 0.1 to 400 mg per day in one or more administrations.

The following Examples illustrate the invention but do not limit it in any way. The starting materials employed are known products or products prepared according to known procedures.

The structures of the compounds described in the Examples were determined according to customary spectrophotometric techniques (infrared, nuclear magnetic resonance, mass spectrometry . . . ).

PREPARATION A tert-Butyl 3-[(diphenoxyphosphoryl)oxy]-4H-1,4-benzoxazine-4-carboxylate Step A: tert-Butyl 2,3-dihydro-4H-1,4-benzoxazin-3-one-4-carboxylate Under an inert atmosphere, 73 mmol of 2H-1,4-benzoxazin-3-one are dissolved in 100 ml of acetonitrile in the presence of 3.65 mmol of 4-dimethylaminopyridine and 80 mmol of di-tert-butyl dicarbonate. The mixture is stirred for 4 hours. After concentration, the residue is taken up in ethyl acetate. The organic phase is washed with a saturated sodium chloride solution, dried over magnesium sulphate, filtered and concentrated. After evaporation of the solvent and purification by chromatography on silica gel (petroleum ether/ethyl acetate: 8/2), the expected product is isolated.
Melting point: 72° C.
IR (KBr): $v_{C=O}$=1713, 1779 cm$^{-1}$; $v_{COC}$=1148 cm$^{-1}$.
Mass spectrum: m/z 250 (M+1).

Step B: tert-Butyl 3-[(diphenoxyphosphoryl)oxy]-4H-1,4-benzoxazine-4-carboxylate Under an anhydrous atmosphere, 12 mmol of TMEDA are added to a solution of 10 mmol of the product obtained in the above Step A in 50 ml of anhydrous THF. After having cooled the solution to −78° C., 12 mmol of 2M LDA (in a heptane/THF solution) are added dropwise. After stirring for 2 hours, 12 mmol of diphenyl chlorophosphate are added dropwise to the reaction mixture, which is maintained at −78° C. for a further 2 hours. After returning to ambient temperature, the solution is hydrolysed and then extracted with ethyl acetate. The organic phase is dried over magnesium sulphate, filtered and concentrated. After purification of the residue by chromatography on silica gel (petroleum ether/ethyl acetate: 9/1), the expected product is isolated.
Melting point: 64° C.
IR (KBr): $v_{C=O}$=1732 cm$^{-1}$; $v_{P=O}$ 1313 cm$^{-1}$.
Mass spectrum: m/z 482 (M+1).

PREPARATION B

Phenyl 3-[(diphenoxyphosphoryl)oxy]-2,3-dihydro-4H-pyrido-[3,2-b][1,4]oxazine-4-carboxylate Step A: Phenyl 2,3-dihydro-4H-pyrido[3,2-b][1,4]oxazin-3-one-4-carboxylate Under an anhydrous atmosphere, a solution of 10 mmol of 2H-pyrido[3,2-b][1,4]oxazin-3-one in 50 ml of tetrahydrofuran is cooled to −78° C. At that temperature, 11 mmol of a 1.6M solution of n-butyllithium in hexane are added dropwise. After 30 minutes' contact at −78° C., 11 mmol of phenyl chloroformate are added dropwise and stirring is maintained for a further 2 hours. After returning to ambient temperature, the solution is hydrolysed and then extracted with ethyl acetate. The organic phase is dried over magnesium sulphate, filtered and evaporated. After purification by chromatography on silica gel (petroleum ether/ethyl acetate: 8/2), the expected product is isolated.
Melting point: 97° C.
IR (KBr): $v_{C=O}$=1717 cm$^{-1}$; 1803 cm$^{-1}$.
Mass spectrum: m/z 271 (M+1).

Step B: Phenyl 3-[(diphenoxyphosphoryl)oxy]-4H-pyrido[3,2-b][1,4]oxazine-4-carboxylate The expected product is obtained in accordance with the procedure described in Step B of Preparation A starting from the compound of the above Step.
Melting point: 82° C.
IR (KBr): $v_{C=O}$=1749 cm$^{-1}$; $v_{P=O}$ 1294 cm$^{-1}$.
Mass spectrum: m/z 503 (M+1).

PREPARATION C 8-(Pinacolboronyl)-1,4-dioxaspiro[4.5]dec-7-ene

Step A: 8-(Trifluoromethyl)sulphonyloxy-1,4-dioxaspiro[4.5]dec-7-ene

Under an anhydrous atmosphere, a 2M solution of 6.4 mmol of LDA in a mixture of THF/heptane is diluted with 8 ml of THF. The temperature is lowered to −78° C. and then 6.4 mmol of 1,4-dioxaspiro[4.5]decan-8-one dissolved in 8 ml of THF are slowly added. The reaction mixture is stirred for 2 hours at that temperature and 9.6 mmol of N-phenyl-trifluoromethanesulphonimide dissolved in 8 ml of THF are added. After stirring for 15 minutes at −78° C. and then returning to ambient temperature for a night, the mixture is concentrated. After purification on neutral alumina gel (petroleum ether/ethyl acetate: 95/5), the expected product is isolated.

IR (NaCl film): $v_{C=C}$=1692 cm$^{-1}$; $v_{SO2}$=1418 cm$^{-1}$.

Step B: 8-(Pinacolboronyl)-1,4-dioxaspiro[4.5]dec-7-ene

Under an inert atmosphere, 0.7 mmol of the product obtained in the above Step A, 1.05 mmol of pinacolborane, 0.028 mmol of bis(triphenylphosphine)palladium(II) chloride, 0.084 mmol of triphenylarsine and 2.1 mmol of triethylamine are mixed in 3 ml of toluene and then heated at 80° C. for 2 hours. After cooling, the residue is taken up in ethyl acetate and washed with a saturated sodium chloride solution. The organic phase is dried over magnesium sulphate, filtered and concentrated. After purification of the residue by chromatography on silica gel (petroleum ether/ethyl acetate: 9/1), the expected product is isolated.

Melting point: 58° C.

IR (KBr): $v_{C=C}$=1635 cm$^{-1}$; $v_{COC}$=1115, 1143 cm$^{-1}$.

Mass spectrum: m/z 267 (M+1).

EXAMPLE 1

8-(tert-Butoxycarbonyl)-2-[2-(dimethylamino)ethyl]-5-hydroxy-2,3-dihydrobenzo[a]pyrrolo[3,4-c]phenoxazine-1,3-dione Step A: tert-Butyl 3-(1,4-dioxaspiro[4.5]dec-7-en-8-yl)-4H-1,4-benzoxazine-4-carboxylat Under an inert atmosphere, a 1M solution of 1 mmol of the product of Preparation A and 5% bis(triphenylphosphine)palladium(II) chloride in tetrahydrofuran is stirred for 10 minutes at ambient temperature. 1.5 mmol of the product of Preparation C, a few drops of ethanol and 2 mmol of a 2M aqueous sodium carbonate solution are added to the reaction mixture, which is then refluxed for one hour. After cooling and hydrolysis, the solution is extracted with ethyl acetate. The organic phase is dried over magnesium sulphate, filtered and concentrated. After purification by chromatography on silica gel (petroleum ether/ethyl acetate: 6/4), the expected product is isolated.

Melting point: 92-93° C.

IR (KBr): $v_{C=O}$=1711 cm$^{-1}$; $v_{COC}$=1113, 1163 cm$^{-1}$.

Mass spectrum: m/z 372 (M+1).

Step B: Dimethyl 12-(tert-butoxycarbonyl)-3,3-(1,2-ethylenedioxy)-1,2,3,4, 4a, 6a-hexahydro-12H-benzo[a]phenoxazine-5,6-dicarboxylate In a closed system, 8 mmol of the product obtained in the above Step A and 40 mmol of dimethyl acetylenedicarboxylate are stirred at 80° C. for 22 hours. After purification by chromatography on silica gel (petroleum ether/ethyl acetate: 7/3), the expected product is isolated.

Melting point: 234-235° C.

IR (KBr): $v_{C=O}$=1728 cm$^{-1}$; $v_{COC}$=1152 cm$^{-1}$.

Mass spectrum: m/z 514 (M+1).

Step C: Dimethyl 12-(tert-butoxycarbonyl)-3,3-(1,2-ethylenedioxy)-1,2,3,4-tetrahydro-12H-benzo[a]phenoxazine-5,6dicarborxylate Under an inert atmosphere, 0.92 mmol of the product obtained in the above Step B and 2.75 mmol of recrystallised N-bromosuccinimide are heated in 23 ml of distilled carbon tetrachloride for 10 minutes at reflux, using a 60 W lamp, in the presence of a catalytic amount of benzoyl peroxide. After cooling, the solution is filtered and then concentrated. After purification by chromatography on silica gel (petroleum ether/ethyl acetate: 6/4), the expected product is isolated.

Melting point: <50° C.

IR (KBr): $v_{C=O}$=1701, 1717, 1733 cm$^{-1}$; $v_{COC}$=1152, 1195 cm$^{-1}$.

Mass spectrum : m/z 512 (M+1).

Step D: Dimethyl 3-oxo-1,3,4,12-tetrahydro-2H-benzo[a]phenoxazine-5,6-dicarboxylate 3 ml of 12M hydrochloric acid are added dropwise to 0.6 mmol of the product obtained in the above Step C dissolved in 3 ml of ethanol. The mixture is stirred for 1.5 hours at ambient temperature. After neutralisation with a saturated sodium hydrogen carbonate solution and extraction with ethyl acetate, the organic phase is dried over magnesium sulphate, filtered and concentrated. After purification by chromatography on silica gel (petroleum ether/ethyl acetate: 5/5 to 0/10), the expected product is isolated.

Melting point: 250-251° C.

IR (KBr): $v_{C=O}$=1695, 1720 cm$^{-1}$; $v_{NH}$=3430 cm$^{-1}$.

Mass spectrum: m/z 366 (M+1).

Step E: Dimethyl 12-(tert-butoxycarbonyl)-3-[(tert-butoxycarbonyl)oxy]-1,2-dihydro-12H-benzo[a]phenoxazine-5,6-dicarboxylate Under an inert atmosphere, 0.69 mmol of the compound obtained in the above Step D is dissolved in 10 ml of tetrahydrofuran. After the addition of 1.73 mmol of 4-dimethyl-aminopyridine and 1.73 mmol of di-tert-butyl dicarbonate, the mixture is stirred for 12 hours. After concentration, the residue is taken up in ethyl acetate and washed twice with a 1M hydrochloric acid solution. The organic phase is dried over magnesium sulphate, filtered and concentrated, allowing the expected product to be obtained.

IR (NaCl film): $v_{C=O}$=1728, 1756 cm$^{-1}$; $v_{COC}$=1139 cm$^{-1}$.

Mass spectrum: m/z 568 (M+1).

Step F: Dimethyl 12-(tert-butoxycarbonyl)-3-[(tert-butoxycarbonyl)oxy]-12H-benzo[a]phenoxazine-5,6-dicarboxylate Under an inert atmosphere, 0.62 mmol of the compound obtained in the above Step E is dissolved in 5 ml of toluene in the presence of 4.96 mmol of 2,3-dichloro-5,6-dicyano-1,4-benzoquinone and the mixture is heated at 90° C. for 24 hours. After cooling and concentration, the reaction mixture is taken up in dichloromethane and washed with an 8% sodium hydroxide solution. The aqueous phase is extracted with dichloromethane and the organic phases are combined, dried over magnesium sulphate, filtered and concentrated. After purification by chromatography on silica gel (petroleum ether/ethyl acetate: 7/3), the expected product is isolated.

Melting point: 101-102° C.

IR(KBr): $v_{C=O}$=1731, 1739, 1756, 1766 cm$^{-1}$; $v_{COC}$=1149 cm$^{-1}$.

Mass spectrum: m/z 566 (M+1).

Step G: Dimethyl 12-(tert-butoxycarbonyl)-3-hydroxy-12H-benzo[a]phenoxazine-5,6-dicarboxylate Under an inert atmosphere, 0.28 mmol of the compound obtained in the above Step F is dissolved in 2 ml of methanol in the presence of 0.34 mmol of sodium methanolate. The mixture is stirred at ambient temperature for 12 hours. After concentration and hydrolysis, the mixture is extracted with ethyl acetate, dried over magnesium sulphate, filtered and evaporated. After purification by chromatography on silica gel (petroleum ether/ethyl acetate: 7/3), the expected product is isolated.

Melting point: 90-91° C. (decomposition).
IR (KBr): $v_{C=O}$=1722 cm$^{-1}$; $v_{COC}$=1152 cm$^{-1}$; $v_{OH}$=3442 cm$^{-1}$.
Mass spectrum: m/z 466 (M+1).

Step H: 8-(tert-Butoxycarbonyl)-2-[2-(dimethylamino) ethyl]-5-hydroxy-2,3-dihydrobenzo[a]pyrrolo[3,4-c]phenoxazine-1,3-dione Under an inert atmosphere, 0.26 mmol of the compound obtained in the above Step G is heated at 100° C. in 4 ml of N,N-dimethylethylenediamine for 7 hours. After cooling, the excess of diamine is evaporated off. After purification by chromatography on silica gel (dichloromethane/methanol: 95/5), the expected product is isolated.
Melting point: 190° C. (degradation).
IR (KBr): $v_{C=O}$=1705, 1762 cm$^{-1}$; $v_{CO}$=1249 cm$^{-1}$; $v_{OH}$=3446 cm$^{-1}$.
Mass spectrum: m/z 490.5 (M+1).

EXAMPLE 2

2-[2-(Dimethylamino)ethyl]-5-hydroxybenzo[a]pyrrolo[3,4-c]phenoxazine-1,3-dione hydrochloride 3 ml of 12M hydrochloric acid are added dropwise to 0.2 mmol of the compound of Example 1 dissolved in 4 ml of ethanol. The reaction mixture is stirred for 1.5 hours at ambient temperature and then concentrated. By addition of ethyl ether, a precipitate is formed which is filtered off, allowing the expected product to be obtained.
IR (KBr): $v_{C=O}$=1686, 1744 cm$^{-1}$; $v_{NH,OH}$=3431 cm$^{-1}$.
Mass spectrum: m/z 390 (M+1).

EXAMPLE 3

8-(tert-Butoxycarbonyl)-2-[2-(dimethylamino)ethyl]-5-(2-hydroxy-ethoxy)-2,3-dihydrobenzo[a]pyrrolo [3,4-c]phenoxazine-1,3-dione Step A: Dimethyl 12-(tert-butoxycarbonyl)-3-(2-hydroxyethoxy)-12H-benzo[a]phenoxazine-5,6-dicarboxylate The expected product is obtained in accordance with the procedure described in Step F of Example 1 starting from the compound of Step B of Example 1.
Melting point: 87-88° C.
IR (KBr): $v_{C=O}$=1725cm$^{-1}$; $v_{OH}$=3440 cm$^{-1}$.
Mass spectrum: m/z 510 (M+1).

Step B. 8-(tert-Butoxycarbonyl)-2-[2-(dimethylamino) ethyl]-5-(2-hydroxyethoxy)-2,3-dihydrobenzo[a ]pyrrolo[3,4-c]phenoxazine-1,3-dione The expected product is obtained in accordance with the procedure described in Step H of Example 1 starting from the compound of the above Step A.
Melting point: >80° C. (degradation).
IR (KBr): $v_{C=O}$=1707, 1763 cm$^{-1}$; $v_{OH}$=3447 cm$^{-1}$.
Mass spectrum: m/z 534 (M+1).

EXAMPLE 4

8-(tert-Butoxycarbonyl)-2-[2-(dimethylamino)ethyl]-5-{2-[(methylsulphonyl)oxy]ethoxy}-2,3-diydrobenzo[a]pyrrolo-[3,4-c]phenoxazine-1,3-dione Under an inert atmosphere, 0.93 mmol of triethylamine and then 0.93 mmol of mesyl chloride are added to a solution of 0.06 mmol of the compound of Example 3 in 3 ml of dichloromethane at 0° C. Stirring is maintained at 0° C. for 8 hours. At ambient temperature, the solution is hydrolysed and then extracted with dichloromethane. The organic phase is dried over magnesium sulphate, filtered and concentrated. After purification by chromatography on silica gel (dichloromethane/methanol: 95/5), the expected product is isolated.
Melting point: 70-80° C. (gum).
IR (KBr): $v_{C=O}$=1707, 1763 cm$^{-1}$.
Mass spectrum: m/z 612 (M+1).

EXAMPLE 5

2-[2-(Dimethylamino)ethyl]-5-{2-[(methylsulphonyl)oxy] ethoxy}-1,2,3,8-tetrahydrobenzo[a]pyrrolo[3,4-c]phenoxazine-1,3-dione 0.03 mmol of the compound of Example 4 is dissolved in 1 ml of formic acid and stirred at ambient temperature for 3 hours. After concentration, the residue is taken up in dichloromethane and washed with a 2M sodium carbonate solution and then with water. The organic phases are combined, dried over magnesium sulphate, filtered and concentrated. After purification by chromatography on silica gel (dichloromethane/-methanol: 9/1), the expected product is isolated.
IR (KBr): $v_{C=O}$=1686, 1702 cm$^{-1}$; $v_{NH}$=3432 cm$^{-1}$.
Mass spectrum: m/z 512 (M+1).

EXAMPLE 6

2-[2-(Dimethylamino)ethyl]-5-(2-hydroxyethoxy)benzo-[a] pyrrolo[3,4-c]phenoxazine-1,3-dione The expected product is obtained according to the procedure of Example 5 starting from the compound of Example 3.
Melting point: 216° C. (gum).
IR (KBr): $v_{C=O}$=1690, 1741 cm$^{-1}$; $v_{NH}$=3427 cm$^{-1}$.
Mass spectrum: m/z 434 (M+1).

EXAMPLE 7

8-(Formyl)-2-[2-(dimethylamino)ethyl]-5-(2-hydroxyethoxy)-benzo[a]pyrrolo[3,4-c]phenoxazine-1,3-dione The expected product is obtained in the course of the purification by chromatography on silica gel of Example 6.
Melting point: 202° C.
IR (KBr): $v_{C=O}$=1693, 1732 cm$^{-1}$; $v_{NH}$=3428 cm$^{-1}$.
Mass spectrum: m/z 462 (M+1).

EXAMPLE 8

8-(Phenoxycarbonyl)-5-(2-hydroxyethoxy)-2-methyl-2,3-dihydrobenzo[e]pyrido[2',3':5,6][1,4]oxazino[3,2-g]isoindole-1,3-dione Step A: Phenyl 3-(1,4-dioxaspiro[4.5]dec-7-en-8-yl)-4H-pyrido[3,2-b][1,4]oxazine-4-carboxylate The expected product is obtained according to the procedure of Step A of Example 1 starting from the compound of Preparation B.
IR (KBr): $v_{C=O}$=1741 cm$^{-1}$; $v_{COC}$=1111, 1197 cm$^{-1}$.
Mass spectrum: m/z 393 (M+1).

Step B: 8-(Phenoxycarbonyl)-5,5-(1,2-ethylenedioxy)-2-methyl-2,3,3a,3b,4,5,6,7, 13a,13b-decahydrobenzo[e]pyrido[2',3':5,6][1,4]oxazino[3,2-g]isoindole-1,3-dione In a closed system, 1 mmol of the product obtained in the above Step A and 3 mmol of N-methylmaleimide are stirred at 95° C. for 2 hours in the presence of a few drops of toluene. After purification by chromatography on silica gel (petroleum ether/ethyl acetate: 6/4), the product is isolated.
Melting point: 150° C. (gum).
IR (KBr): $v_{C=O}$=1701, 1786 cm$^{-1}$.
Mass spectrum: m/z 504 (M+1).

Step C: 8-(Phenoxycarbonyl)-5-(2-hydroxyethoxy)-2-methyl-2,3-dihydrobenzo-[e]pyrido[2',3':5,6][1,4]oxazino[3,2-g]isoindole-1,3-dione The expected product is obtained in accordance with the procedure described in Step C of Example 1 starting from the compound of the above Step B.
Melting point: 250° C. (gum).
IR (KBr): $v_{C=O}$=1707, 1752 cm$^{-1}$; $v_{COC}$=1191 cm$^{-1}$; $v_{OH}$=3463 cm$^{-1}$.
Mass spectrum: m/z 498 (M+1).

EXAMPLE 9

2-[2-(Dimethylamino)ethyl]-5-(2-hydroxyethoxy)benzo[e]pyrido-[2',3':5,6][1,4]oxazino[3,2-g]isoidole-1,3-dione The expected product is obtained in accordance with the procedure described in Step H of Example 1 starting from the compound of Example 8.
Mass spectrum: m/z 435 (M+1).

EXAMPLE 10

8-(tert-Butoxycarbonyl)-2-[2-(diethylamino)ethyl]-5-hydroxy-2,3-dihydrobenzo[a]pyrrolo[3,4-c]phenoxazine-1,3-dione The expected product is obtained in accordance with the procedure described in Step H of Example 1 starting from the compound of Step G of Example 1 and N,N-diethylethylene-diamine.

EXAMPLE 11

2-[2-(Diethylamino)ethyl]-5-hydroxybenzo[a]pyrrolo[3,4-c]-phenoxazine-1,3-dione

The expected product is obtained in accordance with the procedure of Example 2 starting from the compound of Example 10.

PHARMACOLOGICAL STUDY OF THE COMPOUNDS OF THE INVENTION

EXAMPLE 12

In Vitro Activity

L1210 Murine Leukaemia

L1210 murine leukaemia was used in vitro. The cells are cultured in RPMI 1640 complete culture medium containing 10% foetal calf serum, 2 mM glutamine, 50 units/ml of penicillin, 50 μg/ml of streptomycin and 10 mM Hepes, pH=7.4. The cells are distributed on microplates and are exposed to the cytotoxic compounds for 4 doubling periods, or 48 hours. The number of viable cells is then quantified by a colorimetric assay, the Microculture Tetrazolium Assay (J. Carmichael et al., *Cancer Res.*; 47, 939-942 (1987)). The results are expressed as the IC$_{50}$, the concentration of cytotoxic agent that inhibits the proliferation of the treated cells by 50%. All the compounds of the invention exhibit good cytotoxicity with respect to this cell line. By way of example, the compound of Example 2 has an IC$_{50}$ of 0.25 μM with respect to L1210.

Human Cell Lines

The compounds of the invention were also tested on human cell lines originating from solid tumours, in accordance with the same test protocol as that described for L1210 murine leukaemia but with incubation periods of 4 days instead of 2 days. By way of illustration, the compound of Example 2 has an IC$_{50}$ of 0.27 μM with respect to DU145 prostate carcinoma, 0.16 μM with respect to A549 non-small-cell lung carcinoma, 0.6 μM with respect to HT-29 colon carcinoma and 0.26 μM with respect to KB-3-1 epidermoid carcinoma.

Those different results clearly demonstrate the strong anti-tumour potential of the compounds of the invention with respect to leukaemias and solid tumours.

EXAMPLE 13

Action on the Cell Cycle

L1210 cells are incubated for 21 hours at 37° C. in the presence of various concentrations of test compounds. The cells are then fixed by 70% (v/v) ethanol, washed twice in PBS and incubated for 30 minutes at 20° C. in PBS that contains 100 μg/ml of RNAse and 50 μg/ml of propidium iodide. The results are expressed in terms of the percentage of cells that have accumulated in the G2+M phase after 21 hours, compared with the control (control: 20%). The compounds of the invention are of special interest; at a concentration of less than 2.5 μM, they induce accumulation of at least 80% of cells in the G2+M phase after 21 hours.

EXAMPLE 14

In Vivo Activity

Anti-Tumour Activity on P 388 Leukaemia

Line P388 (murine leukaemia) was supplied by the National Cancer Institute (Frederick, USA). The tumour cells (10$^6$ cells) were inoculated on day 0 into the peritoneal cavity of female B6D2F1 mice (Iffa Credo, France). Six mice weighing from 18 to 20 g were used per test group. The products were administered by the intraperitoneal route on day 1. The anti-tumour activity is expressed as % T/C:

$$\% \ T/C \text{(mouse)} = \frac{\text{Median survival time of the treated animals}}{\text{Meadian survival time of the control animals}} \times 100$$

The results obtained show excellent in vivo activity in the P388 leukaemia model, with a T/C of 210% for a dose of 50 mg/kg, along with low toxicity of the compounds, indicating an excellent therapeutic index.

EXAMPLE 15

Pharmaceutical Composition: Injectable Solution

| Compound of Example 2 | 10 mg |
| --- | --- |
| Distilled water for injectable preparations | 25 ml |

The invention claimed is:

1. A compound selected from those of formula (I):

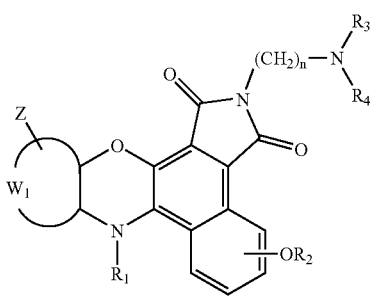

wherein:
- $W_1$ together with the carbon atoms to which it is bonded, represents phenyl or pyridyl,
- Z represents a group selected from hydrogen, halogen, linear or branched $(C_1-C_6)$alkyl, aryl, aryl-$(C_1-C_6)$alkyl in which the alkyl moiety may be linear or branched, aryloxy, aryl-$(C_1-C_6)$alkoxy in which the alkoxy moiety may be linear or branched, hydroxy and linear or branched $(C_1-C_6)$alkoxy,
- $R_1$ represents a group selected from hydrogen, linear or branched $(C_1-C_6)$alkyl, aryl, aryl-$(C_1-C_6)$alkyl in which the alkyl moiety may be linear or branched, —C(O)—$R_5$, or linear or branched $(C_1-C_6)$alkylene substituted by one or more identical or different groups selected from halogen, cyano, —$OR_6$, —$NR_6R_7$, —$CO_2R_6$, —$C(O)R_6$ and —C(O)—$NHR_6$, wherein:
- $R_5$ represents a group selected from hydrogen, linear or branched $(C_1-C_6)$alkyl, hydroxy, linear or branched $(C_1-C_6)$alkoxy, aryl, aryl-$(C_1-C_6)$alkyl in which the alkyl moiety may be linear or branched and aryloxy,
- $R_6$ and $R_7$, which may be identical or different, each represents a group selected from hydrogen, linear or branched $(C_1-C_6)$alkyl, aryl and aryl-$(C_1-C_6)$alkyl in which the alkyl moiety may be linear or branched, or $R_6$ and $R_7$ together, with the nitrogen atom carrying them, form a monocyclic heterocycle that has from 5 to 6 ring atoms, and which optionally contains in the ring system a second hetero atom selected from oxygen and nitrogen,
- $R_2$ represents hydrogen or —$CH_2CH_2O$—$R_8$ wherein:
- $R_8$ represents a group selected from hydrogen, linear or branched $(C_1-C_6)$alkyl, aryl, aryl-$(C_1-C_6)$alkyl in which the alkyl moiety may be linear or branched, —S(O)$_t$—$R_6$ wherein $R_6$ is as defined hereinbefore and t represents integer of from 0 to 2 inclusive or $T_1$—$R_9$ wherein $T_1$ represents linear or branched $(C_1-C_6)$alkylene and $R_9$ represents a group selected from halogen, cyano, —$OR_6$, —$NR_6R_7$, —C(O)H, —C(O)$OR_6$ and —C(O)$NR_6R_7$ wherein $R_6$ and $R_7$ are as defined hereinbefore,
- $R_3$ and $R_4$, which may be identical or different, each represents, a group selected from hydrogen, linear or branched $(C_1-C_6)$alkyl, aryl, aryl-$(C_1-C_6)$alkyl in which the alkyl moiety may be linear or branched, or
- $R_3$ and $R_4$ together, with the nitrogen atom carrying them, form a monocyclic heterocycle that has from 5 to 6 ring atoms and which optionally contains in the ring system a second hetero atom selected from oxygen and nitrogen,
- n represents an integer of from 1 to 6 inclusive, it being understood that:
aryl may be a phenyl, naphthyl, dihydronaphthyl, tetrahydronaphthyl, indenyl or indanyl group, each of those groups being optionally substituted by one or more identical or different groups selected from halogen, linear or branched $(C_1-C_6)$alkyl, linear or branched $(C_1-C_6)$trihaloalkyl, hydroxy, linear or branched $(C_1-C_6)$alkoxy, and amino optionally substituted by one or two linear or branched $(C_1-C_6)$alkyl groups.

2. A compound of claim 1, which is a compound of formula (IA):

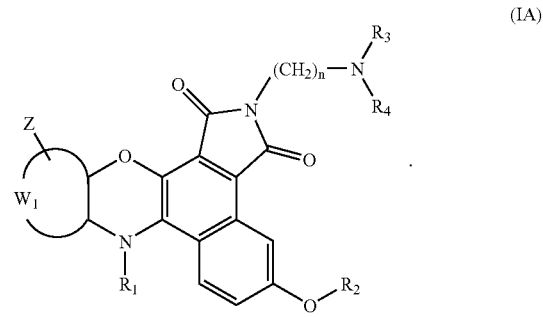

3. A compound of claim 1, which is a compound of formula (IB):

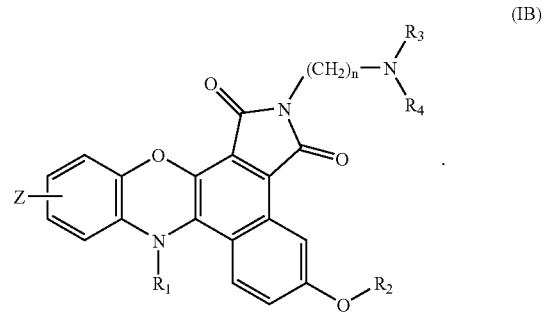

4. A compound of claim 1, which is a compound of formula (IC):

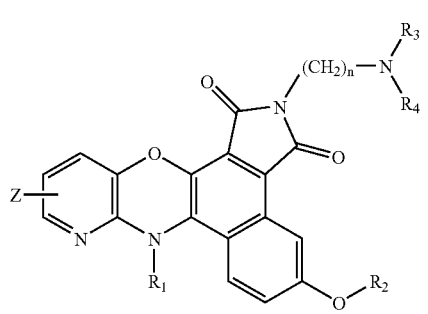

(IC)

5. A compound of claim 1, wherein Z represents hydrogen.

6. A compound of claim 1, wherein $R_1$ represents hydrogen or —C(O)—$R_5$ wherein $R_5$ represents hydrogen.

7. A compound of claim 1, wherein $R_2$ represents hydrogen or —$CH_2CH_2O$—$R_8$ wherein $R_8$ represents hydrogen.

8. A compound of claim 1, wherein n represents 2.

9. A compound of claim 1, wherein $R_3$ and $R_4$, which may be identical or different, each represents a linear or branched ($C_1$-$C_6$)alkyl group.

10. A compound of claim 1, which is selected from:
2-[2-(dimethylamino)ethyl]-5-hydroxybenzo[a]pyrrolo[3,4-c]phenoxazine-1,3-dione,
2-[2-(diethylamino)ethyl]-5-hydroxybenzo[a]pyrrolo[3,4-c]phenoxazine-1,3-dione,
2-[2-(dimethylamino)ethyl]-5-(2-hydroxyethoxy)-2,3-dihydrobenzo[a]pyrrolo[3,4-c]phenoxazine-8-carbaldehyde-1,3-dione,
2-[2-(dimethylamino)ethyl]-5-(2-hydroxyethoxy)benzo[a]pyrrolo[3,4-c]-phenoxazine-1,3-dione,
2-[2-(dimethylamino)ethyl]-5-(2-hydroxyethylmethanesulphonate)-benzo[a]pyrrolo[3,4-c]phenoxazine-1,3-dione, and
2-[2-(dimethylamino)ethyl]-5-(2-hydroxyethoxy)benzo[e]pyrido[2',3':5,6][1,4]-oxazino[3,2-g]isoindole-1,3-dione.

11. A method for treating a living animal body, including a human, afflicted with a condition selected from prostate carcinoma, non-small lung cell carcinoma, colon carcinoma, and epidermoid carcinoma, comprising the step of administering to the living animal body, including a human, an amount of a compound of claim 1, which is effective for alleviation of the condition.

12. A pharmaceutical composition comprising as active principle an effective amount of a compound of claim 1, together with one or more pharmaceutically acceptable excipients or vehicles.

* * * * *

UNITED STATES PATENT AND TRADEMARK OFFICE
CERTIFICATE OF CORRECTION

PATENT NO. : 7,312,213 B2  Page 1 of 1
APPLICATION NO. : 10/531648
DATED : December 25, 2007
INVENTOR(S) : Gerard Coudert et al.

It is certified that error appears in the above-identified patent and that said Letters Patent is hereby corrected as shown below:

Title page, Item (75) Inventor Address: "Boisemont" should be --Le Pecq--.

Title page, Item (73) Assignee: "LES LABORATORIES SERVIER" should be --LES LABORATOIRES SERVIER--.

Signed and Sealed this

Eighth Day of July, 2008

JON W. DUDAS
*Director of the United States Patent and Trademark Office*